US008968268B2

(12) United States Patent
Anderson et al.

(10) Patent No.: US 8,968,268 B2
(45) Date of Patent: Mar. 3, 2015

(54) ANTISEPTIC CAP

(75) Inventors: William Anderson, Cary, IL (US);
Mark Wilson, Rochester, NY (US);
Gary Henniger, Belmar, NJ (US);
Larry Colquitt, West Henrietta, NY (US)

(73) Assignee: Excelsior Medical Corporation, Neptune, NJ (US)

( * ) Notice: Subject to any disclaimer, the term of this patent is extended or adjusted under 35 U.S.C. 154(b) by 0 days.

(21) Appl. No.: 13/456,853

(22) Filed: Apr. 26, 2012

(65) Prior Publication Data
US 2013/0023828 A1 Jan. 24, 2013

Related U.S. Application Data

(63) Continuation of application No. 11/821,190, filed on Jun. 22, 2007, now Pat. No. 8,167,847.

(60) Provisional application No. 60/815,806, filed on Jun. 22, 2006.

(51) Int. Cl.
*A61M 31/00* (2006.01)
*A61M 5/00* (2006.01)
*A61M 5/315* (2006.01)
(Continued)

(52) U.S. Cl.
CPC ........... *A61M 5/31511* (2013.01); *A61M 39/02* (2013.01); *A61M 39/16* (2013.01); *A61M 39/20* (2013.01); *A61M 5/002* (2013.01); *A61M 5/3135* (2013.01); *A61M 5/347* (2013.01); *A61M 39/162* (2013.01); *A61M 2005/3104* (2013.01);
(Continued)

(58) Field of Classification Search
CPC ... A61M 39/20; A61M 39/162; A61M 39/16; A61M 39/165; A61L 2/26
USPC .................. 604/187, 192–195, 197, 199, 206
See application file for complete search history.

(56) References Cited

U.S. PATENT DOCUMENTS

| 877,946 A | 2/1908 | Overton |
| 1,793,068 A | 2/1931 | Dickinson |

(Continued)

FOREIGN PATENT DOCUMENTS

| CA | 2148847 | 12/1995 |
| CA | 2169689 | 8/1996 |

(Continued)

OTHER PUBLICATIONS

Examination Report dated Jun. 6, 2011, issued by the Canadian Intellectual Property Office in connection with Canadian Patent Application No. 2,692,157 (2 pages).

(Continued)

*Primary Examiner* — Aarti B Berdichevsky
*Assistant Examiner* — Bradley Osinski
(74) *Attorney, Agent, or Firm* — McCarter & English, LLP

(57) ABSTRACT

The present invention provides an antiseptic cap for use with an access site having a housing with a wall defining a chamber, the wall having a set of threads on an inner surface of the wall; and an access site contacting surface associated with the housing having an antiseptic substance for contacting a surface of the access site. The present invention also provides an antiseptic cap equipped plunger assembly wherein an antiseptic cap is retained within a housing of the plunger.

10 Claims, 9 Drawing Sheets

(51) Int. Cl.
*A61M 39/02* (2006.01)
*A61M 39/16* (2006.01)
*A61M 39/20* (2006.01)
A61M 5/31 (2006.01)
A61M 5/34 (2006.01)
A61M 39/10 (2006.01)

(52) U.S. Cl.
CPC .............. *A61M2005/31506* (2013.01); *A61M 2039/1033* (2013.01); *A61M 5/3137* (2013.01)
USPC .......................................... 604/513; 604/187

(56) References Cited

U.S. PATENT DOCUMENTS

| | | | |
|---|---|---|---|
| 3,270,743 A | 9/1966 | Gingras | |
| 3,882,858 A | 5/1975 | Klemm | |
| 3,977,401 A | 8/1976 | Pike | |
| 3,987,930 A | 10/1976 | Fuson | |
| 4,041,934 A | 8/1977 | Genese | |
| 4,095,810 A * | 6/1978 | Kulle | 138/96 R |
| 4,243,035 A | 1/1981 | Barrett | |
| 4,280,632 A | 7/1981 | Yuhara | |
| 4,294,370 A | 10/1981 | Toeppen | |
| 4,317,446 A | 3/1982 | Ambrosio et al. | |
| 4,335,756 A | 6/1982 | Sharp et al. | |
| 4,402,691 A | 9/1983 | Rosenthal et al. | |
| 4,417,890 A | 11/1983 | Dennehey et al. | |
| 4,427,126 A | 1/1984 | Ostrowsky | |
| 4,432,764 A | 2/1984 | Lopez | |
| 4,432,766 A | 2/1984 | Bellotti et al. | |
| 4,439,184 A | 3/1984 | Wheeler | |
| 4,440,207 A * | 4/1984 | Genatempo et al. | 150/154 |
| 4,461,368 A | 7/1984 | Plourde | |
| 4,507,111 A | 3/1985 | Gordon et al. | |
| 4,624,664 A * | 11/1986 | Peluso et al. | 604/256 |
| 4,666,057 A | 5/1987 | Come et al. | |
| 4,666,427 A | 5/1987 | Larsson et al. | |
| 4,671,306 A | 6/1987 | Spector | |
| 4,703,762 A | 11/1987 | Rathbone et al. | |
| 4,728,321 A | 3/1988 | Chen | |
| 4,747,502 A | 5/1988 | Luenser | |
| 4,752,983 A | 6/1988 | Grieshaber | |
| 4,778,447 A | 10/1988 | Velde et al. | |
| 4,799,926 A | 1/1989 | Haber | |
| 4,811,847 A | 3/1989 | Reif et al. | |
| 4,927,019 A | 5/1990 | Haber et al. | |
| 4,957,637 A | 9/1990 | Cornell | |
| 4,983,161 A | 1/1991 | Dadson et al. | |
| 4,989,733 A | 2/1991 | Patry | |
| 4,991,629 A | 2/1991 | Ernesto et al. | |
| 5,143,104 A | 9/1992 | Iba et al. | |
| 5,190,534 A | 3/1993 | Kendell | |
| 5,205,821 A | 4/1993 | Kruger et al. | |
| 5,242,425 A | 9/1993 | White et al. | |
| 5,246,011 A | 9/1993 | Caillouette | |
| D342,134 S | 12/1993 | Mongeon | |
| 5,554,135 A | 9/1996 | Menyhay | |
| 5,580,530 A | 12/1996 | Kowatsch et al. | |
| 5,620,088 A | 4/1997 | Martin et al. | |
| 5,694,978 A | 12/1997 | Heilmann et al. | |
| 5,702,017 A | 12/1997 | Goncalves | |
| 5,722,537 A | 3/1998 | Sigler | |
| 5,792,120 A | 8/1998 | Menyhay | |
| 5,810,792 A | 9/1998 | Fangrow, Jr. et al. | |
| 5,820,604 A | 10/1998 | Fox et al. | |
| 5,827,244 A | 10/1998 | Boettger | |
| 5,941,857 A * | 8/1999 | Nguyen et al. | 604/263 |
| 5,954,957 A | 9/1999 | Chin-Loy et al. | |
| 5,971,972 A | 10/1999 | Rosenbaum | |
| D416,086 S | 11/1999 | Parris et al. | |
| 5,989,229 A | 11/1999 | Chiappetta | |
| 6,045,539 A * | 4/2000 | Menyhay | 604/256 |
| 6,116,468 A | 9/2000 | Nilson | |
| 6,117,114 A | 9/2000 | Paradis | |
| 6,126,640 A | 10/2000 | Tucker et al. | |
| 6,202,870 B1 | 3/2001 | Pearce | |
| 6,227,391 B1 | 5/2001 | King | |
| 6,250,315 B1 | 6/2001 | Ernster | |
| 6,394,983 B1 | 5/2002 | Mayoral et al. | |
| 6,679,395 B1 | 1/2004 | Pfefferkorn et al. | |
| 6,827,766 B2 | 12/2004 | Carnes et al. | |
| 7,083,605 B2 | 8/2006 | Miyahara | |
| 7,282,186 B2 | 10/2007 | Lake, Jr. et al. | |
| 7,431,712 B2 | 10/2008 | Kim | |
| 7,516,846 B2 | 4/2009 | Hansen | |
| 7,635,344 B2 | 12/2009 | Tennican et al. | |
| D607,325 S | 1/2010 | Rogers et al. | |
| 7,731,678 B2 | 6/2010 | Tennican et al. | |
| 7,731,679 B2 | 6/2010 | Tennican et al. | |
| 7,749,189 B2 | 7/2010 | Tennican et al. | |
| 7,753,891 B2 | 7/2010 | Tennican et al. | |
| 7,763,006 B2 | 7/2010 | Tennican | |
| 7,766,182 B2 | 8/2010 | Trent et al. | |
| 7,776,011 B2 | 8/2010 | Tennican et al. | |
| 7,780,794 B2 | 8/2010 | Rogers et al. | |
| 7,794,675 B2 | 9/2010 | Lynn | |
| 7,799,010 B2 | 9/2010 | Tennican | |
| 7,857,793 B2 | 12/2010 | Raulerson et al. | |
| 7,922,701 B2 | 4/2011 | Buchman | |
| 7,959,026 B2 | 6/2011 | Bertani | |
| 7,985,302 B2 | 7/2011 | Rogers et al. | |
| 7,993,309 B2 | 8/2011 | Schweikert | |
| 8,162,899 B2 | 4/2012 | Tennican | |
| 8,167,847 B2 | 5/2012 | Anderson et al. | |
| 8,206,514 B2 | 6/2012 | Rogers et al. | |
| 8,231,602 B2 | 7/2012 | Anderson et al. | |
| 8,273,303 B2 | 9/2012 | Ferlic et al. | |
| 8,361,408 B2 | 1/2013 | Lynn | |
| 8,480,968 B2 | 7/2013 | Lynn | |
| 8,647,326 B2 | 2/2014 | Solomon et al. | |
| 2002/0193752 A1 | 12/2002 | Lynn | |
| 2003/0153865 A1 | 8/2003 | Connell et al. | |
| 2004/0034042 A1 | 2/2004 | Tsuji et al. | |
| 2004/0215148 A1 | 10/2004 | Hwang et al. | |
| 2004/0258560 A1 | 12/2004 | Lake, Jr. et al. | |
| 2005/0013836 A1 | 1/2005 | Raad | |
| 2005/0065479 A1 | 3/2005 | Schiller et al. | |
| 2005/0124970 A1 | 6/2005 | Kunin et al. | |
| 2005/0147524 A1 | 7/2005 | Bousquet | |
| 2005/0203460 A1 | 9/2005 | Kim | |
| 2005/0214185 A1 | 9/2005 | Castaneda | |
| 2006/0030827 A1 | 2/2006 | Raulerson et al. | |
| 2007/0112333 A1 * | 5/2007 | Hoang et al. | 604/533 |
| 2007/0167910 A1 | 7/2007 | Tennican et al. | |
| 2007/0249996 A1 | 10/2007 | Tennican et al. | |
| 2007/0265578 A1 | 11/2007 | Tennican et al. | |
| 2007/0282280 A1 | 12/2007 | Tennican | |
| 2008/0019889 A1 | 1/2008 | Rogers et al. | |
| 2008/0027399 A1 | 1/2008 | Harding et al. | |
| 2008/0039803 A1 | 2/2008 | Lynn | |
| 2008/0058733 A1 | 3/2008 | Vogt et al. | |
| 2008/0086091 A1 | 4/2008 | Anderson et al. | |
| 2008/0095680 A1 | 4/2008 | Steffens et al. | |
| 2008/0132880 A1 | 6/2008 | Buchman | |
| 2008/0177250 A1 | 7/2008 | Howlett et al. | |
| 2008/0235888 A1 | 10/2008 | Vaillancourt et al. | |
| 2009/0008393 A1 | 1/2009 | Howlett et al. | |
| 2009/0012426 A1 | 1/2009 | Tennican | |
| 2009/0062766 A1 | 3/2009 | Howlett et al. | |
| 2009/0093757 A1 | 4/2009 | Tennican | |
| 2009/0099529 A1 | 4/2009 | Anderson et al. | |
| 2009/0205151 A1 | 8/2009 | Fisher et al. | |
| 2009/0259194 A1 | 10/2009 | Pinedjian et al. | |
| 2010/0049170 A1 | 2/2010 | Solomon et al. | |
| 2010/0064456 A1 | 3/2010 | Ferlic | |
| 2010/0160894 A1 | 6/2010 | Julian et al. | |
| 2010/0172794 A1 | 7/2010 | Ferlic et al. | |
| 2010/0242993 A1 | 9/2010 | Hoang et al. | |
| 2010/0306938 A1 | 12/2010 | Rogers et al. | |
| 2011/0030726 A1 | 2/2011 | Vaillancourt et al. | |
| 2011/0232020 A1 | 9/2011 | Rogers et al. | |
| 2011/0265825 A1 | 11/2011 | Rogers et al. | |
| 2011/0277788 A1 | 11/2011 | Rogers et al. | |

(56) References Cited

U.S. PATENT DOCUMENTS

| | | | |
|---|---|---|---|
| 2012/0195807 | A1 | 8/2012 | Ferlic |
| 2012/0216359 | A1 | 8/2012 | Rogers et al. |
| 2012/0216360 | A1 | 8/2012 | Rogers et al. |
| 2012/0283693 | A1 | 11/2012 | Anderson et al. |
| 2012/0302997 | A1 | 11/2012 | Gardner et al. |

FOREIGN PATENT DOCUMENTS

| | | |
|---|---|---|
| CA | 2583601 | 4/2006 |
| CA | 2626864 | 5/2007 |
| CA | 2651192 | 11/2007 |
| CA | 2615146 | 6/2008 |
| CN | 2402327 Y | 10/2000 |
| CN | 201150420 Y | 11/2008 |
| DE | 29617133 | 1/1997 |
| EP | 0108785 | 5/1984 |
| EP | 0227219 | 7/1987 |
| EP | 0245872 | 11/1987 |
| EP | 0769265 | 4/1997 |
| EP | 1061000 | 12/2000 |
| EP | 1331020 | 7/2003 |
| EP | 1977714 | 10/2008 |
| FR | 2493149 A | 5/1982 |
| FR | 2782910 | 3/2000 |
| GB | 123221 | 2/1919 |
| GB | 2296182 | 6/1996 |
| GB | 2333097 | 7/1999 |
| GB | 2387772 | 10/2003 |
| JP | H04-99950 | 3/1992 |
| JP | 2002-291906 | 10/2002 |
| RU | 2246321 | 2/2005 |
| WO | WO 9812125 | 3/1998 |
| WO | WO 2004/112846 A2 | 12/2004 |
| WO | WO 2006/007690 | 1/2006 |
| WO | WO 2007/137056 A2 | 11/2007 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/039171 | 4/2010 |
| WO | WO 2011/119021 | 9/2011 |

OTHER PUBLICATIONS

Examination Report dated Apr. 27, 2011, issued by the Canadian Intellectual Property Office in connection with Canadian Patent Application No. 2,692,157 (3 pages).
Examination Report dated Jan. 23, 2013, issued by the Canadian Intellectual Property Office in connection with Canadian Patent Application No. 2,692,157 (4 pages).
Notice of Allowance dated Oct. 2, 2013, issued by the Canadian Intellectual Property Office in connection with Canadian Patent Application No. 2,692,157 (1 page).
Office Action dated Oct. 2012, issued by the Intellectual Property Office of Colombia in connection with Colombian Patent Application No. 10.000.937 (9 pages).
Examination Report dated Jun. 13, 2011, issued by the Intellectual Property Office of New Zealand in connection with New Zealand Patent Application No. 582395 (2 pages).
Examination Report and Notice of Acceptance of Complete Specification dated Dec. 5, 2012, issued by the Intellectual Property Office of New Zealand in connection with New Zealand Patent Application No. 582395 (1 page).
Interview Summary dated Nov. 18, 2010, from pending U.S. Appl. No. 11/821,190 (4 pages).
Notice of Allowance dated Jul. 29, 2011, from U.S. Appl. No. 11/821,190 (6 pages).
Notification of First Office Action dated Aug. 3, 2011, issued by the State Intellectual Property Office of the People's Republic of China in connection with Chinese Patent Application No. 200880103854.5 (5 pages).
International Search Report of the International Searching Authority mailed Sep. 11, 2008, issued in connection with International Patent Application No. PCT/US08/07797 (2 pages).
Written Opinion of the International Searching Authority mailed Sep. 11, 2008, issued in connection with International Patent Appln. No. PCT/US08/07797 (3 pages).
Office Action dated Jun. 9, 2011 from U.S. Appl. No. 12/214,526 (7 pages).
Final Office Action dated Oct. 31, 2011 from U.S. Appl. No. 12/214,526 (8 pages).
Interview Summary dated Mar. 23, 2012 from U.S. Appl. No. 12/214,526 (3 pages).
Redacted version of letter from David A. Divine, Esq. of Lee & Hayes, dated May 27, 2011 (3 pages).
Redacted version of letter from David A. Divine, Esq. of Lee & Hayes, dated May 16, 2011 (3 pages).
Photographs of the Baxter Minicap (Sep. 1, 1998) (4 pages).
Office Action dated Dec. 21, 2011 from U.S. Appl. No. 13/095,516 (27 pages).
Office Action dated Dec. 17, 2009 from U.S. Appl. No. 11/821,190 (10 pages).
Office Action dated Aug. 2, 2010 from U.S. Appl. No. 11/821,190 (14 pages).
Office Action dated Mar. 7, 2011 from U.S. Appl. No. 11/821,190 (16 pages).
Notice of Allowance dated Apr. 26, 2011 from U.S. Appl. No. 11/821,190 (9 pages).
Second Office Action dated Apr. 16, 2012, along with English translation, issued by the State Intellectual Property Office of the People's Republic of China in connection with Chinese Patent Application No. 200880103854.5 (4 pages).
Third Office Action dated Nov. 1, 2012, along with English translation, issued by the State Intellectual Property Office of the People's Republic of China in connection with Chinese Patent Application No. 200880103854.5 (4 pages).
Non-final office action dated Dec. 3, 2013 from U.S. Appl. No. 13/113,777 (13 pages).
Notice of Allowance dated May 16, 2012 from U.S. Appl. No. 13/095,516 (18 pages).
Non-final Office Action dated Feb. 8, 2013 from U.S. Appl. No. 13/473,057 (20 pages).
Final Office Action dated Dec. 3, 2013 from U.S. Appl. No. 13/473,057 (19 pages).
Examination Report No. 3 dated May 1, 2013, issued by the Intellectual Property Office of Australia in connection with Australian Patent Application No. 2008269133 (3 pages).
Preliminary Report on Patentability dated Dec. 22, 2009, in connection with International Patent Application No. PCT/US08/07797 (4 pages).
Non-final Office Action dated May 3, 2013 from U.S. Appl. No. 13/649,569 (15 pages).
Final Office Action dated Aug. 23, 2013 from U.S. Appl. No. 13/649,569 (19 pages).
International Search Report of the International Searching Authority mailed Oct. 26, 2012, issued in connection with International Patent Application No. PCT/US2012/037772 (5 pages).
Written Opinion of the International Searching Authority dated Oct. 26, 2012, issued in connection with International Patent Appln. No. PCT/US2012/037772 (7 pages).
International Preliminary Report on Patentability dated Nov. 26, 2013, issued in connection with International Patent Application No. PCT/US2012/037772 (1 page).
International Search Report of the International Searching Authority dated Nov. 19, 2012, issued in connection with International Patent Application No. PCT/US2012/038880 (5 pages).

(56) References Cited

OTHER PUBLICATIONS

Written Opinion of the International Searching Authority dated Nov. 19, 2012, issued in connection with International Patent Appln. No. PCT/US2012/038880 (8 pages).
International Preliminary Report on Patentability dated Nov. 20, 2013, issued in connection with International Patent Application No. PCT/US2012/038880 (1 page).
Memo concerning Official Action dated Feb. 25, 2013, issued in connection with Mexican Application No. MX/a/2010/000171 (2 pages).
Second Memo concerning Official Action mailed Oct. 22, 2013, issued in connection with Mexican Application No. MX/a/2010/000171 (1 page).
Examination Report dated Nov. 8, 2012, issued by the Intellectual Property Office of New Zealand in connection with New Zealand Patent Application No. 603404 (2 pages).
Examination Report dated Apr. 18, 2013, issued by the Intellectual Property Office of Australia in connection with Australian Patent Application No. 2012258435 (4 pages).
Innovation Patent Examination Report No. 1 dated Apr. 18, 2013, issued by the Intellectual Property Office of Australia in connection with Australian Patent Application No. 2013100345 (3 pages).
Menyhay, et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).
International Standard, "Conical fittings with 6% (Luer) Taper for Syringes, Needles and Certain Other Medical Equipment—Part 2: Lock Fittings" Ref. No. ISO 594-2: 1998. International Organization for Standardization (Sep. 1, 1998) 2nd ed. (16 pages).
Notice of Acceptance dated Nov. 14, 2013, issued by the Intellectual Property Office of Australia in connection with Australian Patent Application No. 2008269133 (2 pages).
Examination Report dated Nov. 8, 2012, issued by the Intellectual Property Office of New Zealand in connection with New Zealand Patent Application No. 582395 (2 pages).
Examinantion Report No. 1 dated Aug. 27, 2012, issued by the Intellectual Property Office of Australia in connection with Australian Patent Application No. 2008269133 (4 pages).
Examination Report No. 2 dated Jan. 9, 2013, issued by the Intellectual Property Office of Australia in connection with Australian Patent Application No. 2008269133 (3 pages).
Non-final Office Action dated Apr. 14, 2014 from U.S. Appl. No. 13/649,569 (27 pages).
International Search Report of the International Searching Authority mailed Feb. 14, 2013, issued in connection with International Patent Application No. PCT/US2012/062078 (3 pages).
Written Opinion of the International Searching Authority mailed Feb. 14, 2013, issued in connection with International Patent Appln. No. PCT/US2012/062078 (3 pages).
International Preliminary Report on Patentability mailed May 6, 2014, issued in connection with International Patent Application No. PCT/US2012/062078 (4 pages).
First Examination Report dated Apr. 8, 2014, issued by the Intellectual Property Office of New Zealand in connection with New Zealand Patent Application No. 623139 (1 page).
First Examination Report dated Apr. 9, 2014, issued by the Intellectual Property Office of New Zealand in connection with New Zealand Patent Application No. 623141 (1 page).
Final Office Action dated Aug. 25, 2014 from U.S. Appl. No. 13/113,777 (9 pages).
First Office Action dated May 4, 2014, along with English translation, issued by the State Intellectual Property Office of the People's Republic of China in connection with Chinese Patent Application No. 201310087320.0 (20 pages).
International Search Report of the International Searching Authority mailed Jul. 28, 2014, issued in connection with International Patent Application No. PCT/US2014/23140 (3 pages).
Written Opinion of the International Searching Authority mailed Jul. 28, 2014, issued in connection with International Patent Appln. No. PCT/US2014/23140 (6 pages).

\* cited by examiner

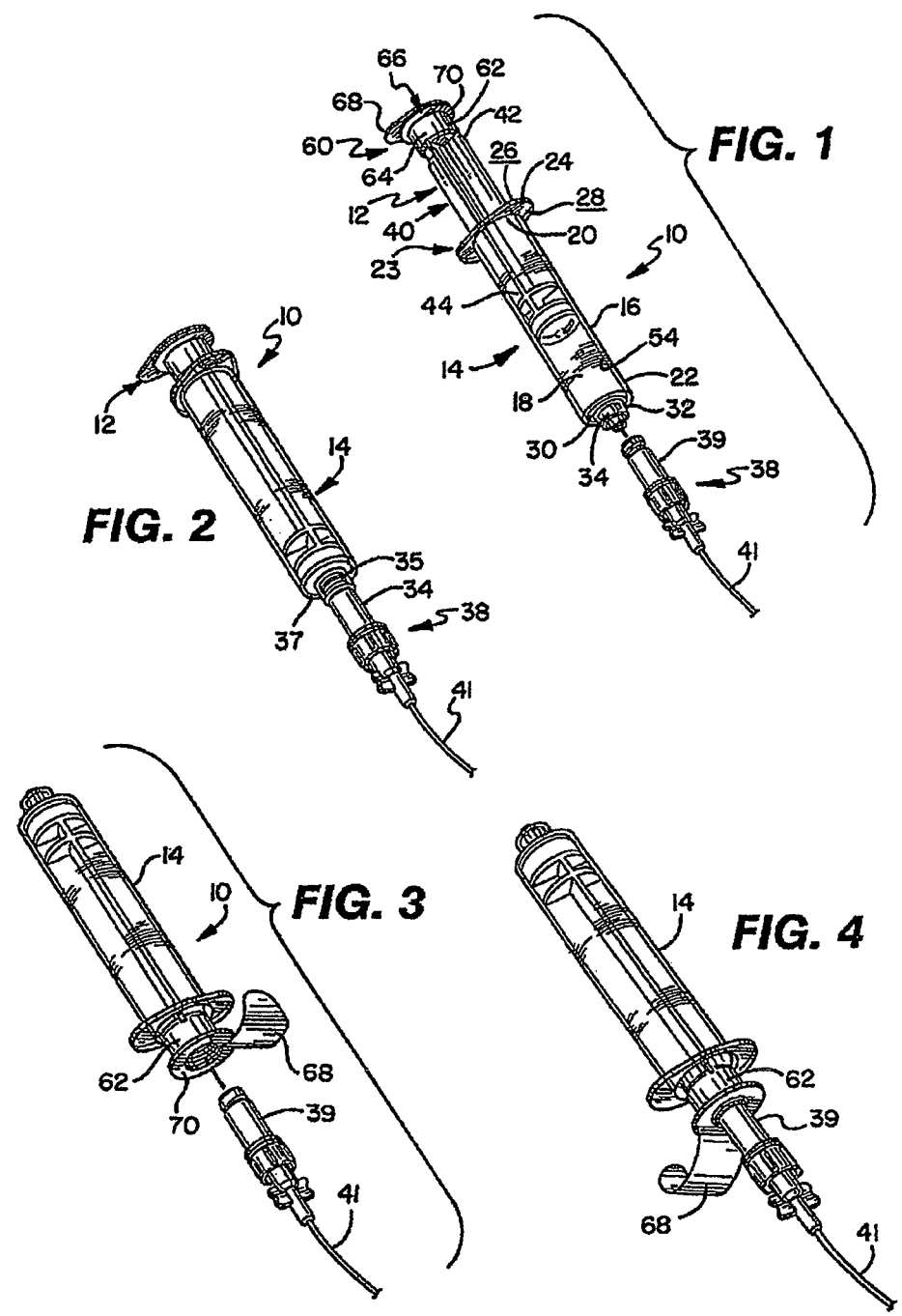

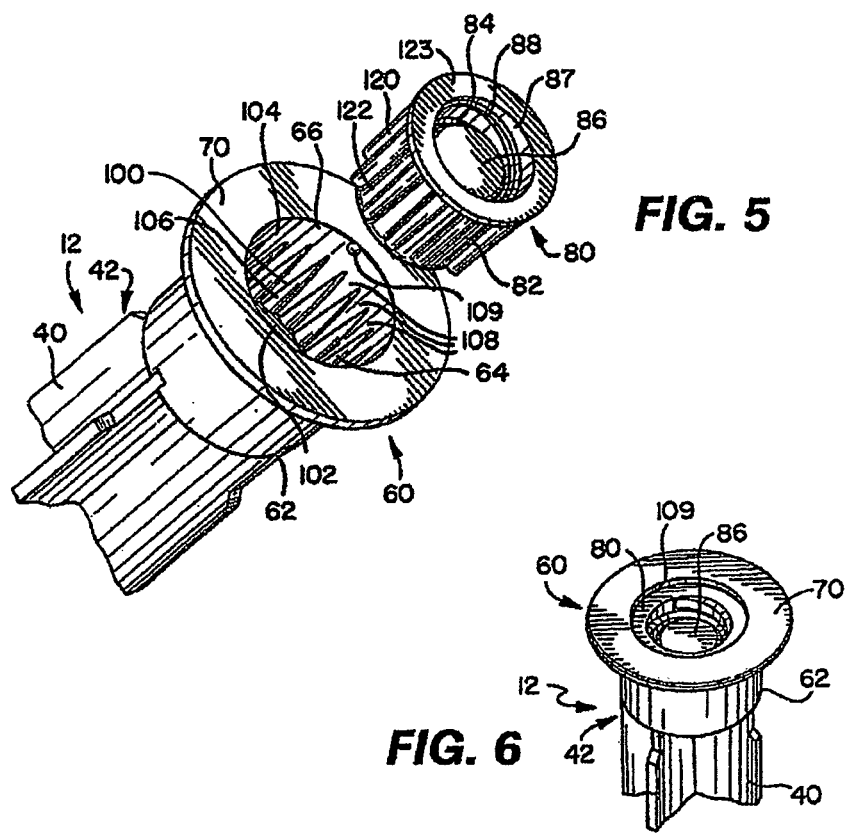
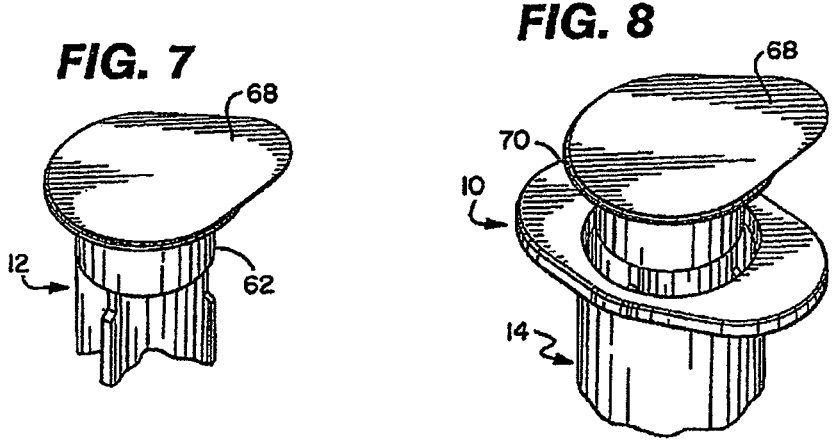

ANTISEPTIC CAP

CROSS-REFERENCE TO RELATED APPLICATIONS

This application is a continuation of U.S. patent application Ser. No. 11/821,190, now U.S. Pat. No. 8,167,847 filed on Jun. 22, 2007, which claims the benefit of U.S. Provisional Application Ser. No. 60/815,806 filed on Jun. 22, 2006, the entire disclosures of which are all expressly incorporated herein by reference.

BACKGROUND OF THE INVENTION

1. Technical Field

The present invention relates to an antiseptic cap and an antiseptic cap equipped syringe plunger assembly and more particularly to an antiseptic cap for attaching to a portion of an indwelling, central venous catheter and delivering an antiseptic composition or liquid to a lumen of the catheter.

2. Background Art

Catheters are widely used to treat patients requiring a variety of medical procedures. Catheters can either be acute, or temporary, for short-term use or chronic for long-term treatment. Catheters are commonly inserted into central veins (such as the vena cava) from peripheral vein sites to provide access to a patient's vascular system. Catheters offer many advantages for patients; for example, chronic catheters provide ready access without repeated punctures or repeated vessel cannulation for administration of large volumes of fluids, nutrients and medications and for withdrawal of blood on an intermittent basis. With respect to the use of catheters for infusion of fluids, examples include the infusion of drugs, electrolytes or fluids used in chemotherapy. In chemotherapy, catheters are used for infusion of drugs on an intermittent basis, ranging from daily to weekly. Another example includes the use of catheters in hyperalimentation treatment, wherein the catheters are usually used for infusion of large volumes of fluids.

For hemodialysis, catheters are commonly used—usually three times per week—for aspiration of blood for dialysis treatment and rapid return of the blood to circulation after treatment. Although a preferred mode of vascular access for a hemodialysis patient involves using an arteriovenous (AV) fistula of either the upper or lower extremities or an arteriovenous "bridge" graft (typically utilizing PTFE), use of these access devices is not always possible or desirable. When either of these modes of vascular access is not available, for example, due to a paucity of adequate blood vessels for creation of AV "shunts" or due to nonoptimally functioning established AV shunts, a large bore venous line catheter is typically required for hemodialysis. Catheters used for hemodialysis usually include two relatively large diameter lumens (usually molded as one catheter) for aspiration and rapid return of blood required during the hemodialysis procedure. One lumen of such a catheter is used for aspiration, or removal, of blood, while the other lumen is used for returning the blood to the patient's bloodstream.

Catheter connections, such as, for example, connections of catheters to dialysis machine tubing, to IV line tubing, to infusion ports and to catheter caps, which are used to seal the end of a catheter to protect the sterility of the catheter and prevent fluid loss and/or particle contamination, are most often made utilizing the medical industry's standardized Luer taper fittings. These fittings, which may either be male couplings or female couplings, include a tapered end of standardized dimensions. Coupling is made by the press-fit of mating parts. A threaded lock-fit or other type of securing mechanism is commonly utilized to ensure the integrity of the pressure fit of the Luer fittings.

Catheters, especially chronic venous catheters, provide challenges in their use. One such challenge is that such catheters can become occluded by a thrombus. In order to prevent clotting of catheters in blood vessels between uses, such as, for example, between dialysis treatments when the catheter is essentially nonfunctioning and dwells inside a "central" vein (i.e. superior vena cava, inferior vena cava, iliac, etc.), the lumens of the catheter are often filled with a lock solution of a concentrated solution of the commonly used anticoagulant, heparin (up to 10,000 units of heparin per catheter lumen).

As used herein, the terms "lock solution" or "locking solution" refer to a solution that is injected or otherwise infused into a lumen of a catheter with the intention of allowing a substantial portion of the lock solution to remain in the lumen and not in the systemic blood circulation until it is desired or required to access that particular lumen again, typically for additional treatment, i.e., infusion or withdrawal of fluid. In addition, attention has been given to the development of alternative lock solutions with the goal of improving the patency rates of vascular catheters. For example, lower-alcohol containing locking solutions are under development wherein the lower alcohols include ethanol, propanol and butanol. Antimicrobial and or anticoagulant additives can optionally be added to the lower-alcohol containing locking solution. Preferably the lock solution can remain in the lumen for a desired amount of time lasting from about 1 hour to 3 or 4 days or longer.

For the reasons set forth above, significant care must be taken when infusing medications, nutrients and the like into a catheter, and when "locking" a catheter between uses, to minimize the risks associated with an indwelling catheter, including the risk of thrombosis or clotting, the risk of excessive anticoagulating and the risk of infection. Syringes are typically used to administer the required amount of catheter lock solution (determined by the catheter manufacturer) into an indwelling catheter after a given use. Flush procedures also require that care be taken to prevent blood reflux into the catheter. Reflux in I.V. therapy is the term commonly used to describe the fluid that is drawn back into the catheter after a flush procedure. The concern is that the reflux fluid contains blood or solution that could cause the catheter to occlude. To ensure that reflux does not occur, flush procedures suggest two techniques: 1) at the end of the flush solution delivery, the user maintains pressure on the syringe plunger while clamping the I.V. line; or 2) while delivering the last 0.5 ml of flush solution disconnect the syringe from the I.V. port or clamp the I.V. line. Either technique maintains positive pressure on the fluid in the catheter to prevent reflux of fluid and blood.

Another concern in catheter care is the prevention of infections. Once source of infections can be through germs that enter the blood stream from the open end of the catheter. Various techniques are known in the art of blocking the exit of the catheter to prevent the refluxing of blood up the catheter and to close the system off from general atmosphere. Certain closures are straight-forward screw-caps that fit over the luer end of the catheter. Others are complex valving systems that may reduce reflux during detachment of the syringes or other connections. Others are pre-slit septums that seal together when the syringe or connected device is removed.

Current procedures to reduce contamination of a catheter, during connection and disconnection, is to swab the connection hub with a disinfectant such as an alcohol. This procedure is prone to human error such as failing to allow sufficient between swabbing and closing of the catheter. Further, sometimes the swabbing step is skipped all together.

In light of the above-described problems, there is a continuing need for advancements in catheter lock techniques, devices and procedures to improve the safety and efficacy of catheter locking procedures, the cleanliness and disinfection of catheter connections and of overall patient care.

BRIEF DESCRIPTION OF THE DRAWINGS

FIG. 1 is a perspective view of an antiseptic cap equipped plunger and syringe barrel assembly prior to connection of a syringe tip to an access point to a central venous catheter;

FIG. 2 is a perspective view of an antiseptic cap equipped plunger and syringe barrel assembly with the syringe tip connected to an access point to a central venous catheter and the plunger assembly is fully depressed within the syringe barrel;

FIG. 3 is a perspective view of an antiseptic cap equipped plunger and syringe barrel assembly prior to connection of the antiseptic cap to an access point to a central venous catheter;

FIG. 4 is a perspective view of an antiseptic cap equipped plunger and syringe barrel assembly after connection of the antiseptic cap to an access point to a central venous catheter;

FIG. 5 is a perspective view assembly drawing of an antiseptic cap equipped plunger;

FIG. 6 is a perspective view of an antiseptic cap equipped plunger in a partially assembled state;

FIG. 7 is a perspective view of the antiseptic cap equipped plunger of FIG. 6 with a top seal;

FIG. 8 is a perspective view of an antiseptic cap equipped plunger of FIG. 7 mounted in a lumen of a syringe barrel;

DETAILED DESCRIPTION OF THE INVENTION

Figure 9:
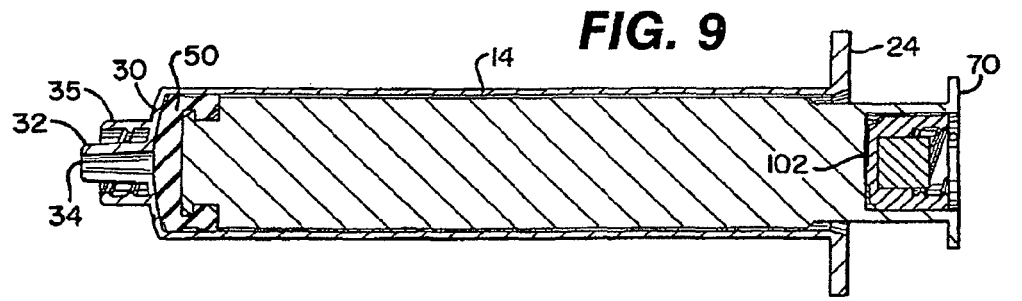
FIG. 9 is a side view in cutaway of an antiseptic cap equipped plunger and syringe barrel assembly.
Figure 10:
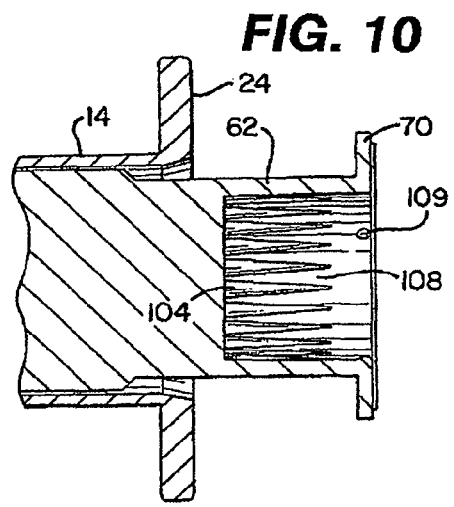
FIG. 10 shows an exploded view of a detail of FIG. 9 of one embodiment of the antiseptic cap equipped plunger and syringe barrel assembly without the cap inserted.

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

FIGS. 1 and 2 show an antiseptic cap equipped plunger and syringe barrel assembly 10 having an antiseptic cap equipped plunger (or piston) assembly 12 and a syringe barrel 14. The barrel 14 has a side wall 16 defining a chamber 18 and the barrel has a proximal end 20 and a distal end 22. The proximal end 20 has an opening 23 to the chamber 18 and a flange 24 extending radially outwardly from the wall 16. The flange 24 has upper and lower surfaces 26, 28 and provides gripping surfaces for a user of the assembly 10. The distal end 22 of the barrel 14 has an end wall 30 and an elongate tip 32 extending distally therefrom and having a passageway 34 therethrough and in fluid communication with the chamber 18. The distal end wall 30, in one preferred form of the invention, is generally conically shaped and, as is well known in the art, can have a locking luer collar 35 concentrically surrounding the tip 32 and having a set of threads 37 on an inside surface thereof. The luer collar 35 allows for attaching a needle or a cannula to the syringe assembly and for docking the assembly to mating threads located on other devices such as valves and injection sites. FIG. 1 shows the syringe assembly proximate an access site 38 having a valve 39 controlling access to a lumen of a tubing 41.

In one preferred form of the invention the chamber 18 of the syringe assembly will be filled with a locking solution or a flush solution for use with an indwelling, central venous catheter. The manner of using a locking or flush solution with a catheter is well known in the art. Suitable locking or flushing solutions will be set forth below. The flush or locking solution is injected into a fluid access site of the catheter to clean and disinfect the catheter and can be withdrawn from the catheter or allowed to remain in an end portion of the catheter to serve as a barrier to the ingress of pathogens and contaminants.

The antiseptic cap plunger assembly 12 has an elongate shaft 40, a proximal end 42 and a distal end 44. The elongate shaft 40, in one preferred form of the invention, is generally cruciform in cross-sectional shape. A stopper or piston 50 is connected to the distal end 44 of the plunger 12. The piston 50 is dimensioned such that when inserted into the syringe barrel chamber 18 an outer circumferential surface of the piston is in fluid-tight engagement with an inner surface 54 of the syringe barrel. The piston assembly 12 when moved proximally (or when being withdrawn) can draw fluid into the chamber and when moved distally (or when inserted into the syringe chamber) can drive fluid out of the chamber. FIG. 1 shows the piston assembly 12 partially inserted into the syringe chamber and FIG. 2 shows the piston assembly fully inserted into the syringe chamber to deliver fluid to the tubing 41.

A housing 60 is located at the proximal end of the plunger assembly 12 and has a wall 62 defining a chamber 64 having an open end 66 which can be sealed by any suitable structure or material such as a cap or by a foil material 68. An optional annular flange 70 extends radially outwardly from the wall 62 and provides a surface upon which the sealing structure can be attached.

FIG. 5 shows a cap assembly 80 proximate the chamber 64 of the housing 60 and FIG. 6 shows the cap assembly 80 within the chamber 64. In one preferred form of the invention, the cap assembly 80 has a cap 82 defining a chamber 84 containing an absorbent material 86 such as a sponge. The sponge 86, in a preferred form of the invention, is wetted or soaked with an agent such as an antiseptic, anticoagulant or antimicrobial and can be selected from the locking and flushing solutions set forth below. The cap 82 has an interior surface 87 with a set of threads 88 for mating with a set of threads on the access site 39.

FIGS. 7 and 8 show the cap assembly 80 sealed with a foil material or lid stock material 68 which can be attached to the flange 70 by any suitable method such as by adhesives or by conductive or inductive heat sealing techniques. FIG. 7 shows the antiseptic cap piston assembly 12 and FIG. 8 shows the antiseptic cap equipped piston assembly 12 inserted into the chamber of the syringe barrel 14 to define the antiseptic cap equipped piston and syringe barrel assembly 10.

FIGS. 3 and 4 show one possible method for utilizing the cap assembly 80 by docking with the valve 39. FIG. 3 shows the lid stock 68 pealed away from the flange 70 and FIG. 4 shows docking the antiseptic cap to the valve 39. The syringe barrel with be rotated clockwise or counterclockwise to engage the threads 88 of the antiseptic cap assembly 80 to the threads of the access site 38. After engagement the syringe barrel will be moved away from the access site 38 and the antiseptic cap 80 will slide outward from the housing 60 and remain docked to the access site 39. The antiseptic cap assembly 80 can be allowed to remain docked to the valve 39 for any suitable period of time from a few minutes to numerous hours. When the antiseptic cap assembly 80 is docked to the valve 39 the tubing or catheter 41 is sealed to block the ingress into the catheter of pathogens and contaminants and the access site is exposed to the antiseptic material in the sponge 86.

It is desirable that during the rotation of the syringe barrel that the antiseptic cap assembly 80 does not rotate with respect to the housing and/or optionally that the plunger assembly 12 does not rotate with respect to the syringe barrel 14 so that the threads 88 of the antiseptic cap can fully engage the threads of the access site. The present invention provides a mechanism associated with the assembly 10 for preventing the rotation of the antiseptic cap assembly 80 with respect to the plunger assembly 12 and more preferably a mechanism on either the plunger assembly or on the antiseptic cap 80 to prevent relative rotational movement between the antiseptic cap 80 and the plunger assembly 12. In an even more preferred form of the invention, the mechanism for preventing relative rotation of the antiseptic cap 80 with respect to the plunger assembly 12 has mating portions on both parts that when assembled cooperatively engage one another to prevent relative rotation. It is also contemplated that a separate mechanism, device or member could be used to lock the two parts together to achieve this purpose.

If a user of the assembly 10 grasps the assembly 10 by the antiseptic cap and plunger assembly 12 then the interlocking structures between the piston assembly 12 and the syringe barrel 14 would not necessarily be needed. Accordingly, FIGS. 5, 9-11 show exemplary structures for locking the antiseptic cap assembly 80 inside the housing 60 so that these parts rotate together and one part does not rotate in a direction or at a rate different from that of the other part. Further, FIGS. 15-18 show exemplary structures for interlocking the antiseptic cap plunger assembly 12 with the syringe barrel 14.

In one preferred form of the invention the housing 60 will have a feature or structure that forms an interference fit with an external surface of the antiseptic cap 80. Even more preferably, the internal surface of the side wall 62 of the housing will have a feature or structure to form an interference fit with a portion of the antiseptic cap 80. In another preferred form of the invention the antiseptic cap will have a feature to form an interference fit with the housing 60 and even more preferably the outer surface of the antiseptic cap 80 will have a feature to contact the inner surface of the housing side wall 62.

In another preferred form of the invention the housing and the cap each have a feature or structure that cooperatively engage one another to prevent relative rotation of the cap 80 and the housing 60. FIG. 5 shows one preferred form of the invention having a plurality of circumferentially spaced and axially extending ribs 100 on the internal surface 87 of the housing side wall (internal ribs 100) for engaging the wall 62 of the antiseptic cap to lock the cap in place to prevent rotation of the cap when positioned inside the housing 60. In a preferred form of the invention, the internal ribs 100 extend from a bottom wall 102 up to an intermediate height of the housing sidewall 62. In a preferred form of the invention the internal ribs 100 will have a height roughly equal to a height of the cap 82. A plurality of internal slots 108 are defined between each set of adjacent internal ribs 100. The internal ribs 100, in a preferred form of the invention, will have a width that tapers inwardly from proximate the bottom wall 102 to a top 104 of the internal ribs so that the width of the internal ribs decrease from a bottom 106 of a rib to the top 104 of the rib. Also, it is preferable that the top of the internal ribs have a generally arcuate profile to act as a lead-in during insertion of the antiseptic cap into the housing 60. Also, extending from the internal surface 87 of the cap 82 is detent 109 positioned proximate a top portion of the side wall 62.

Figure 11:
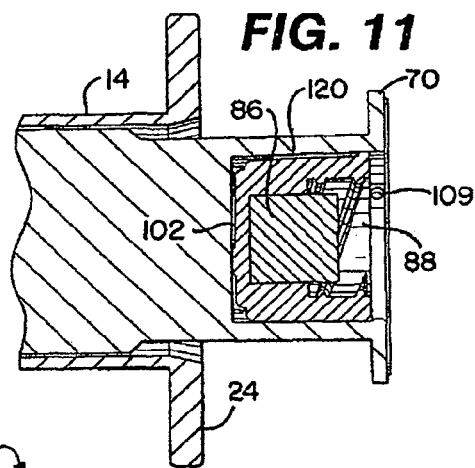
FIG. 11 shows an exploded view of a detail of FIG. 9 of another embodiment of the antiseptic cap equipped plunger and syringe barrel assembly with the cap inserted.

The antiseptic cap 82 has a plurality of circumferentially spaced and axially extending ribs 120 extending along an external surface 122 of the cap 82 (external ribs 120) from an annular flange 123. The external ribs 120 are dimensioned for engaging a portion of the interior wall of the housing 62 to prevent relative rotation of the cap and the plunger assembly 12 and define a plurality of external slots one of each between each adjacent pair of external ribs. When the cap 82 is positioned within the chamber 64 (FIGS. 9 and 11) each of the external ribs 120 are positioned within an internal slot 108 and each of the internal ribs are positioned within an external slot to lock together these parts to assure that the cap rotates in the same direction as the plunger rod. FIGS. 6 and 11 also show that when the cap 82 is positioned within the housing

60, the detent 109 contacts the annular flange 123 to hold the cap in the housing to prevent or resist inadvertent dropping of the cap from the housing prior to docking of the cap with the access site. In one preferred form of the invention, the external ribs 120 are specifically designed in conjunction with internal slots 108 so that the antiseptic cap is guided out of the storage chamber 64 as the cap is screwed onto the threads of the access site.

Figure 12:
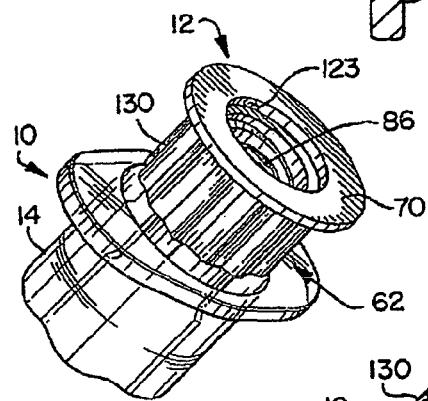
FIGS. 12-14 show various embodiments of grips of the antiseptic cap equipped plunger assembly.
Figure 13:
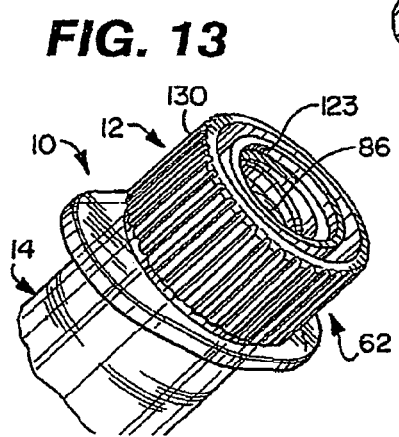
Figure 14:
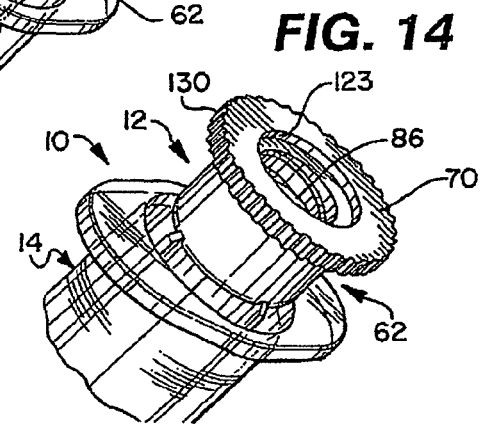
Figure 15:
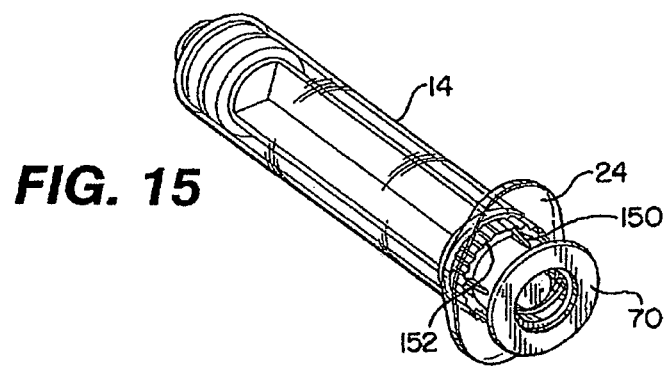
FIGS. 15-17 show various views of one embodiment antiseptic cap equipped plunger and syringe barrel assembly with a barrel lock to resist rotation of the plunger assembly with respect to the syringe barrel.
Figure 16:
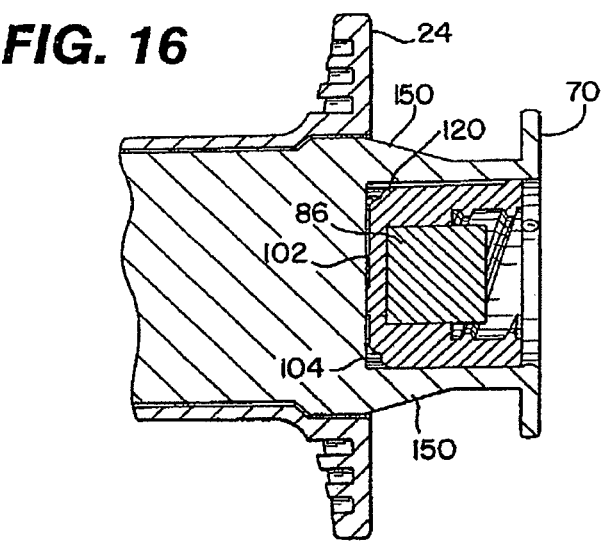
Figure 17:
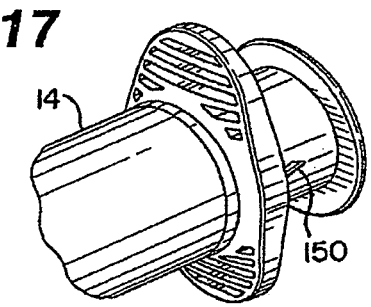

FIGS. 12-14 show several embodiments of gripping surfaces on the housing 60 to facilitate use of the assembly 10 or the plunger assembly 12. FIG. 12 shows axially extending and circumferentially spaced protuberances 130 on an outer surface of the wall 62. The protuberances 130 can have numerous different cross-sectional shapes including circular, polygonal, oval and irregular and, in a preferred form of the invention, extend from the flange 70 to a bottom of the housing.

FIG. 13 shows a housing 60 that has no flange 70 and has protuberances 130 on the wall 62 extending substantially the entire height of the housing 60. FIG. 14 shows a housing 60 where the outer surface of the wall 62 is relatively smooth but has a series of circumferentially spaced and axially extending protuberances 130 on a circumferential edge of the flange 70.

As with the cap and plunger assembly rotational locking features or structures, the optional plunger assembly and syringe barrel locking feature or structure can be positioned alone on the plunger assembly 12, or alone on the syringe barrel or have cooperating structures on both the plunger assembly 12 and the syringe barrel. It is also contemplated that a separate mechanism, device or member could be used to lock the two parts together to achieve this purpose.

FIGS. 15-18 show various embodiments for the optional feature of locking the plunger assembly 12 from rotational motion with respect to the syringe barrel 14. In one embodiment shown in FIGS. 15-17 and 21 a wing 150 extending axially along an outside surface of the housing side wall 62 engages a tooth 152 positioned on an interior surface of the syringe barrel at is proximal end. More preferably, the plunger assembly 12 will have more than one wing 150 with each wing being circumferentially spaced from the other. In an even more preferred form of the invention the plunger assembly will have four wings 150 spaced 90 degrees from one another. Also, in a more preferred form of the invention, the syringe barrel will have a plurality of circumferentially spaced teeth. When the plunger assembly is nearly fully inserted into the syringe barrel each of the wings will extend into a tooth to prevent rotation of the plunger assembly 12 with respect to the syringe barrel 14.

Figure 18:
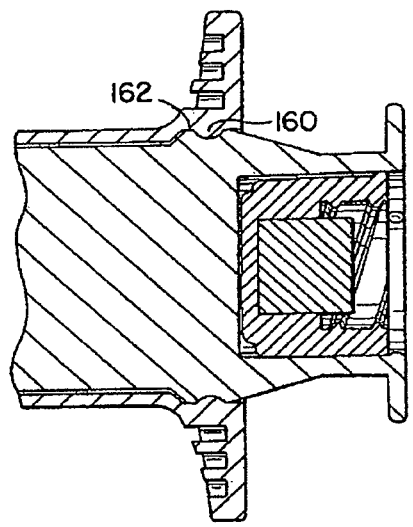
FIG. 18 shows another embodiment of a barrel lock to resist rotation of the plunger assembly with respect to the syringe barrel.

FIG. 18 shows another embodiment of a locking feature to prevent rotation of the plunger assembly 12 with respect to the syringe barrel 14. In this embodiment an annular protuberance 160 positioned on an interior surface of the syringe barrel at its proximal end engages an annular detent 162 on an outside surface of the plunger rod. This captures the plunger rod such that reflux is reduced.

Figure 19:
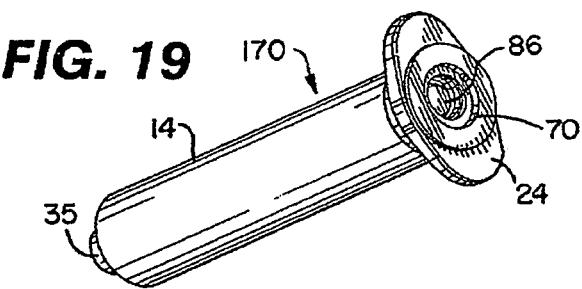
FIGS. 19-20 show various views of another embodiment antiseptic cap equipped plunger and anti-reflux syringe barrel assembly with a barrel lock to resist rotation of the plunger assembly with respect to the syringe barrel.
Figure 20:
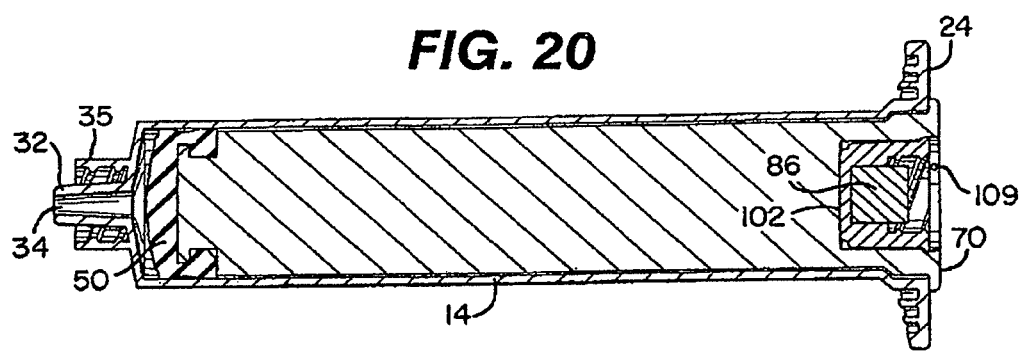
Figure 21:
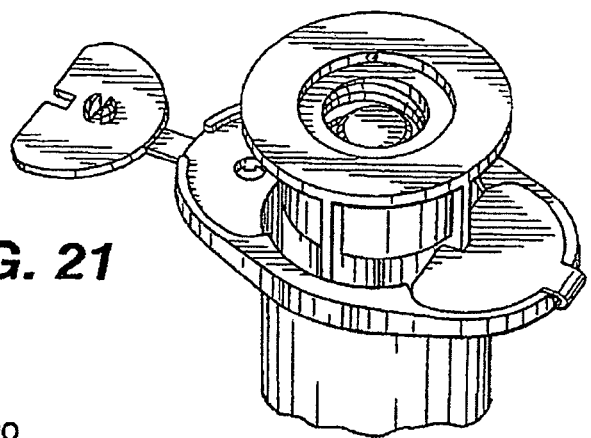
FIG. 21 shows a perspective view of another embodiment antiseptic cap equipped plunger and syringe barrel assembly with a barrel lock to resist rotation of the plunger assembly with respect to the syringe barrel.

FIGS. 19 and 20 show an antiseptic cap equipped plunger assembly and non-refluxing syringe assembly 170. There are numerous methodologies for reducing reflux while utilizing the access site of a central venous catheter. In this embodiment the flange 70 of the plunger assembly 12 abuts the flange 24 of the syringe barrel prior to the piston 50 contacts an interior surface of the syringe end wall 30.

Figure 22A:
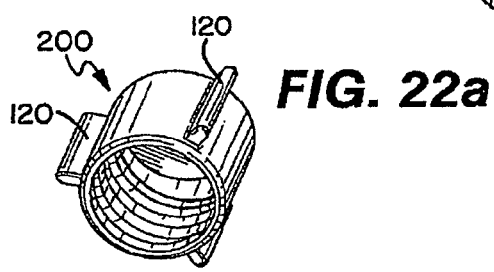
FIGS. 22a,b are respectively a perspective view of an antiseptic cap without a sponge and with a sponge.
Figure 22B:
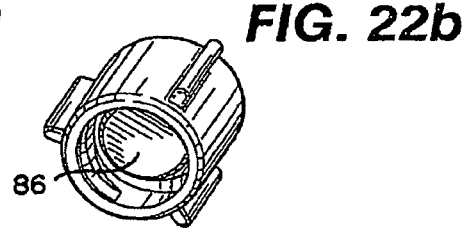
Figure 23:
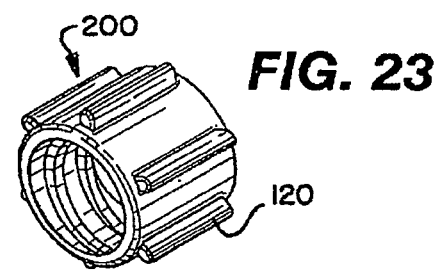
FIGS. 23 and 24 are different embodiments of the antiseptic cap with varying gripping features.
Figure 24:
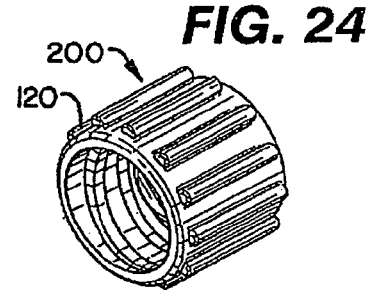

It is contemplated that the antiseptic cap 80 of the present invention need not be coupled or combined with a plunger or a piston. FIGS. 22a, b show an antiseptic cap 200 having three circumferentially spaced ribs 120 for grasping by the hand of a user of the cap. FIG. 22a shows the cap without a sponge and FIG. 22b shows the cap with a sponge. The cap 200 can be used for the same purposes of the cap 80 described above but will be assembled to the catheter by hand. All other features of the cap 200 are essentially the same as described above with the exception that the cap 200 does not have to be dimensioned to fit within a chamber carried by a syringe plunger. FIGS. 23 and 24 show varying frequency of ribs 120 and varying shapes and sizes.

Figure 25:
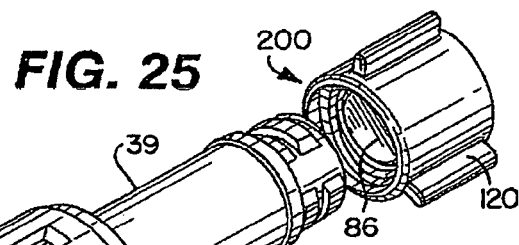
FIG. 25 is a perspective view of the antiseptic cap of FIG. 22b prior to docking with a valve.
Figure 26:
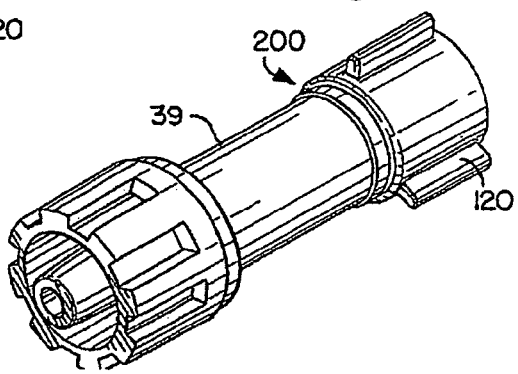
FIG. 26 is a perspective view of the antiseptic cap of FIG. 22b docked with a valve.
Figure 27:
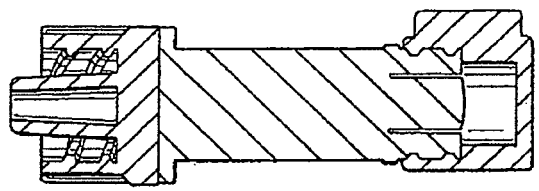
FIG. 27 is a side view in cutaway of the antiseptic cap and valve assembly shown in FIG. 26.

FIG. 25 shows the cap 200 proximate the valve 39 and FIGS. 26 and 27 show the cap 200 docked to the valve 39.

Figure 28:
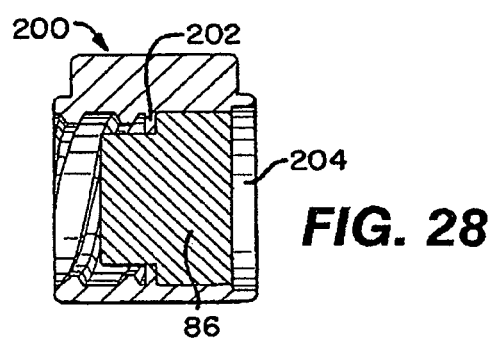
FIGS. 28-30 are side views in cutaway of two different embodiments of the antiseptic cap.
Figure 29:
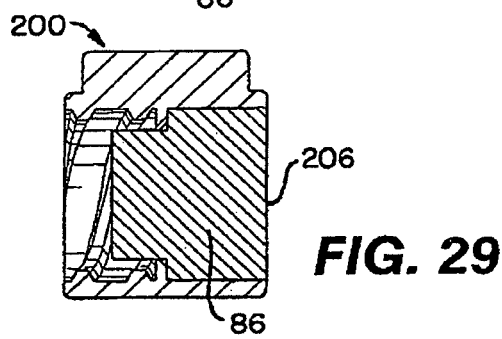
Figure 30:
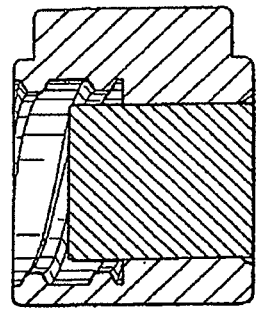

Suitable sponges of the present invention can include any sponge suitable for use for medical purposes and can be naturally occurring or synthetic. The sponges can be die cut into suitable shapes or can be molded into the desired shape. It is desirable that the sponge 86 be attached to the antiseptic cap to prevent the sponge from inadvertently falling out of the cap. FIG. 28 shows the cap 200 is captured between an annular wall 202 and a disc 204 attached to the cap by any suitable method such as ultrasonic or vibrational welding or other techniques well known in the art. FIGS. 29 and 30 show a variation on the cap of FIG. 28 and holds the sponge in place with a plastic sheet 206 heat welded to the cap. In one preferred form of the invention the sponge is attached by an adhesive or by other method to form an assembly which is then attached to the cap.

Figure 31A:
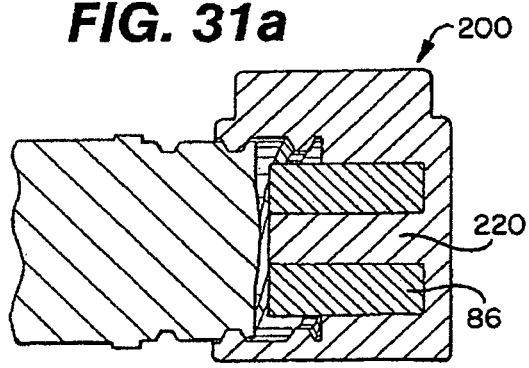
FIGS. 31a,b are, respectively, side views in cutaway showing an antiseptic cap with a centrally disposed actuation post mounted on a valve with the valve in the unactivated and activated positions.
Figure 31B:
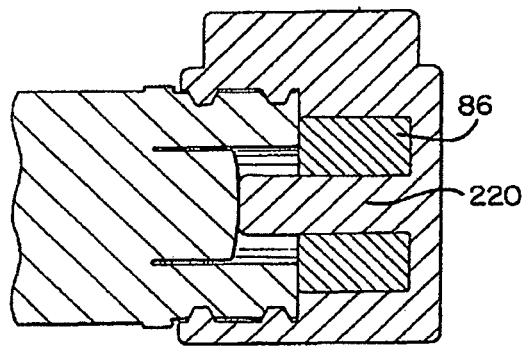

FIGS. 31a, b show the cap 200 having a coaxially disposed and axially extending actuating post 220 circumferentially surrounded by a sponge 86 having a centrally positioned hole to fit over the post 220. FIG. 31a shows the cap 200 in initial engagement with the access site 39 and FIG. 31b shows the cap threaded onto the access site 39 and the actuating post opens the valve 39 an antiseptic fluid is allowed to flow into the valve.

Figure 32:
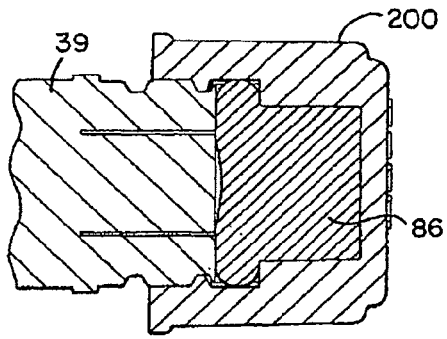
FIGS. 32 and 33 are side views in cutaway showing two different embodiments of an antiseptic cap having a molded sponge.
Figure 33:
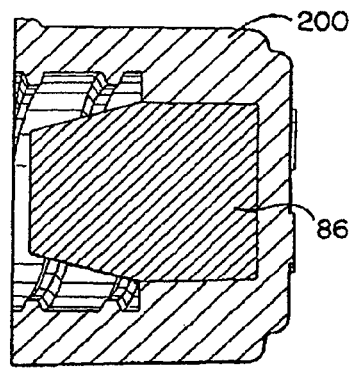
Figure 34:
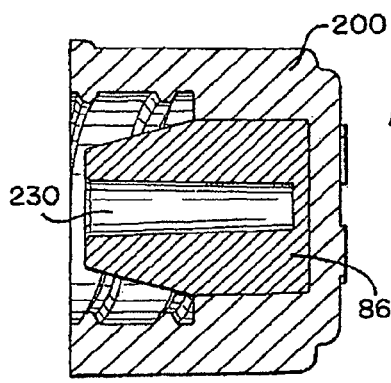
FIG. 34 is a side view in cutaway showing another embodiment of an antiseptic cap having a molded sponge docked to a valve.
Figure 35:
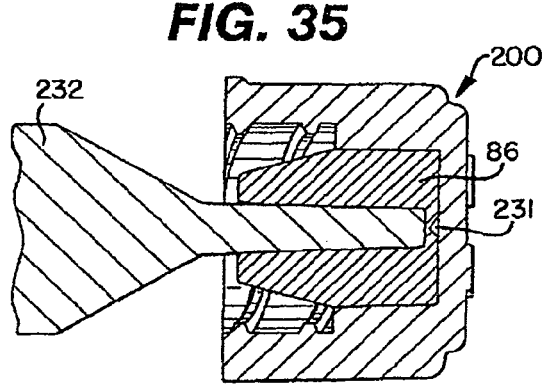
FIG. 35 is a side view in cutaway showing a step of attaching a molded sponge to an antiseptic cap.
Figure 36:
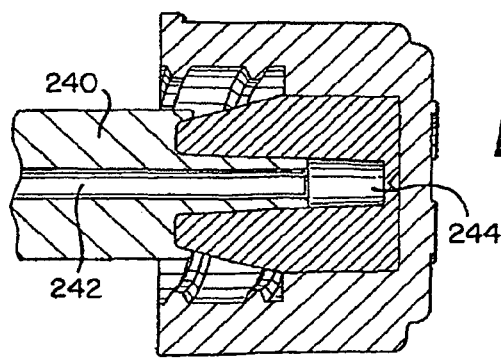
FIG. 36 is a side view in cutaway showing a step of delivering an antiseptic compound to a molded sponge positioned within a cap.

FIGS. 32-34 show varying shaped sponges that, in one preferred form of the invention, were molded into various desirable shapes. The sponge of FIG. 34 has a central opening 230 to facilitate attaching the sponge to the cap and to filling the sponge with antiseptic, anticoagulant or other suitable fluids set forth herein. FIG. 35 shows the cap having a centrally disposed energy director 231 an ultrasonic welder 232 being brought into cooperative engagement with the sponge on a side of the sponge opposite the energy director 231. By applying ultrasonic energy the energy director melts and attaches the sponge to the cap. FIG. 36 shows a filling device 240, having a lumen 242 and a dispensing head 244 in fluid communication with a source of antiseptic, anticoagulant or the like for dispensing a metered amount of such fluid into the interior portion of the sponge.

Figure 37:
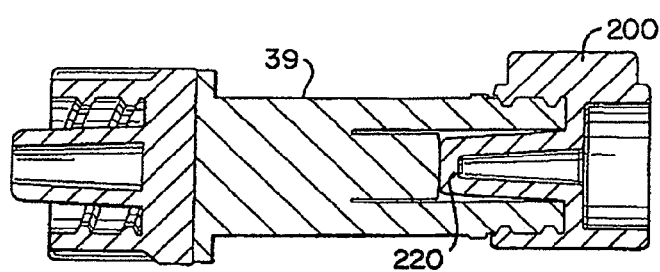
FIG. 37 shows a side view in cutaway of an antiseptic cap docking to a valve with the antiseptic cap having an antiseptic coating.

FIG. 37 shows an alternative embodiment of the antiseptic cap 200 where the sponge is replaced by an antiseptic coating on the actuating post 220 and/or around the entire internal and/or external surface of the cap.

Figure 38:
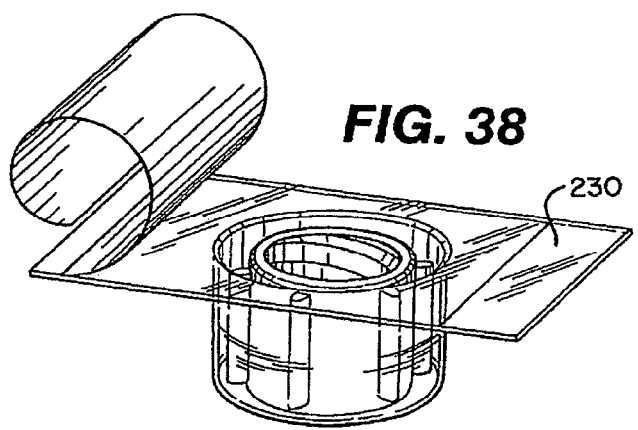
FIG. 38 shows a perspective view of an antiseptic cap in a blister package.

When the cap is not incorporated into the plunger assembly, many packaging options exist. One such embodiment, FIG. 38, shows the antiseptic cap 200 positioned in a blister pack 230 prior to sealing the blister pack.

The syringe barrel and plunger can be fabricated from any material suitable for its purpose and includes glass and polymeric material. Suitable polymeric materials include, but are not limited to, homopolymers, copolymers and terpolymers formed from monomers such as olefins, cyclic olefins, amides, esters, and ethers. The polymeric material may be a blend of more than one polymeric material and can be a monolayer structure or a multilayer structure. In one preferred form of the invention the syringe barrel and the plunger are injection molded from a polypropylene material.

The piston 50 can be formed from any suitable material including a polymeric material, natural or synthetic rubber or a silicone material. The stopper can be selected from a material with a desired durometer so that reflux is reduced when the stopper engages an inner surface of the distal end wall of the syringe barrel.

Suitable locking and flush solutions for filling inside the syringe barrel and/or for soaking the sponge 86 include a lower alcohol selected from ethanol, propanol and butanol. The locking solution can be a single lower alcohol or a blend of lower alcohols.

Suitable locking solutions can also include a lower alcohol with an antimicrobial and or an anticoagulant. Thus, the locking solution can have a single component, two components or more than two components. Suitable locking solutions can contain at least one lower alcohol in a range from 1% to 99% by volume and at least one other anti-microbial and/or anti-coagulant compound in a range from 1% to 99% by volume. The lower alcohol will usually be in aqueous solution, typically at 1% to 99% by volume, usually from 5% to 95% by volume. The at least one other anti-microbial is selected from the group consisting of taurolidine and triclosan, and the at least one anti-coagulant is selected from the group consisting of riboflavin, sodium citrate, ethylene diamine tetraacetic acid, and citric acid.

In one preferred form of the invention, the syringe assembly 10 will be pre-filled with one of the locking solutions and will be packaged by a manufacture and shipped to a health care provider. A cannula or needle will be attached to the distal end of the barrel and placed into fluid communication with the fluid access site of an indwelling central venous catheter. The flush solution will be injected into the catheter to clean or lock the catheter. Afterwards, the cap assembly 80 will be removed from the plunger 17 and the cap will be docked to the fluid access site of the catheter.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. An antiseptic cap assembly for use with an access site comprising:
    a cap having a generally cylindrical side wall defining a chamber having an open upper end and an end wall closing the opposite end, the cap having a substantially flat outer bottom surface and an upper flange extending radially outward from the generally cylindrical side wall, the generally cylindrical side wall having a set of threads on an inner surface of the generally cylindrical side wall and a plurality of circumferentially spaced cap ribs on an external surface of the generally cylindrical side wall extending radially outward from and axially along the generally cylindrical side wall from the bottom surface to the upper flange of the cap;
    an absorbent material within the cap having an antiseptic substance for contacting a distal surface of the access site;
    a housing for receiving the cap, the housing having housing ribs on an inner surface of the housing corresponding to the cap ribs on the cap to prevent relative rotation between the housing and the cap; and
    a seal on the housing to seal the cap in the housing.

2. The cap assembly of claim 1 wherein the absorbent material is positioned within the chamber against the end wall.

3. The cap assembly of claim 2 wherein the antiseptic substance is a liquid and the liquid is releasably retained within the absorbent material.

4. The cap of claim 1 wherein the absorbent material is attached to the housing by welding.

5. The cap of claim 1 wherein the antiseptic substance comprises a lower alcohol.

6. An antiseptic cap for use with an access site comprising:
    a housing having a generally cylindrical side wall defining a chamber having an open upper end and an end wall closing the opposite end, the generally cylindrical side wall having a first diameter, the housing having a substantially flat outer bottom surface and an upper annular flange including an end on the generally cylindrical side wall and a wall extending away from the generally cylindrical side wall, the upper annular flange having a second diameter greater than the first diameter of the generally cylindrical side wall, the generally cylindrical side wall extending from the bottom surface to the open upper end, the generally cylindrical side wall having a set of threads on an inner surface of the generally cylindrical side wall, and a plurality of circumferentially spaced ribs on an external surface of the generally cylindrical side wall extending radially outward from and axially along an outermost peripheral surface of the generally cylindrical side wall at regular intervals about the entire cylindrical side wall from the bottom surface to the upper annular flange of the housing; and
    an absorbent material within the housing having an antiseptic substance for contacting a distal surface of the access site.

7. The cap of claim 6 wherein the absorbent material is positioned within the chamber against the end wall.

8. The cap of claim 6 wherein the antiseptic substance is a liquid and the liquid is releasably retained within the absorbent material.

9. The cap of claim 6 wherein the absorbent material is attached to the housing by welding.

10. The cap of claim 6 wherein the antiseptic substance comprises a lower alcohol.

* * * * *